(12) United States Patent  (10) Patent No.: US 7,520,864 B2
Yeh et al.  (45) Date of Patent: Apr. 21, 2009

(54) MUSCLE STRETCH SENSOR

(75) Inventors: Syh-Shiuh Yeh, Hsinchu (TW);
Chin-Chu Sun, Hsinchu (TW);
Mao-Feng Tu, Hsinchu (TW)

(73) Assignee: Industrial Technology Research Institute (TW)

( * ) Notice: Subject to any disclaimer, the term of this patent is extended or adjusted under 35 U.S.C. 154(b) by 5 days.

(21) Appl. No.: 11/067,130

(22) Filed: Feb. 25, 2005

(65) Prior Publication Data

US 2006/0149167 A1 Jul. 6, 2006

(30) Foreign Application Priority Data

Dec. 28, 2004 (TW) .............. 93141048 A

(51) Int. Cl.
*A61B 5/103* (2006.01)
*A61B 5/117* (2006.01)
*A61B 5/04* (2006.01)
*A61F 2/48* (2006.01)
*A61F 2/70* (2006.01)

(52) U.S. Cl. ............. 600/587; 600/595; 600/372; 600/384; 600/391; 623/24; 623/25

(58) Field of Classification Search ......... 600/587, 600/595, 372, 384, 391; 623/24–25
See application file for complete search history.

(56) References Cited

U.S. PATENT DOCUMENTS

| | | | | |
|---|---|---|---|---|
| 3,418,661 A | * | 12/1968 | Allison et al. | 623/25 |
| 3,942,516 A | * | 3/1976 | Glynn et al. | 600/545 |
| 4,158,196 A | * | 6/1979 | Crawford, Jr. | 340/825.19 |
| 5,037,376 A | * | 8/1991 | Richmond et al. | 600/26 |
| 5,376,128 A | * | 12/1994 | Bozeman, Jr. | 623/24 |
| 5,540,235 A | * | 7/1996 | Wilson | 600/554 |
| 6,344,062 B1 | * | 2/2002 | Abboudi et al. | 623/24 |
| 2003/0093129 A1 | * | 5/2003 | Nicolelis et al. | 607/45 |
| 2005/0010127 A1 | * | 1/2005 | Calderon et al. | 600/546 |
| 2006/0009700 A1 | * | 1/2006 | Brumfield et al. | 600/504 |
| 2006/0136055 A1 | * | 6/2006 | Michel | 623/6.37 |
| 2006/0258961 A1 | * | 11/2006 | Zamierowski et al. | 600/587 |

* cited by examiner

*Primary Examiner*—Max Hindenburg
*Assistant Examiner*—Jeffrey G Hoekstra
(74) *Attorney, Agent, or Firm*—Cameron H. Tousi; Venable LLP

(57) ABSTRACT

The methods and devices of a multi-functional operating interface for a care-taking machine. The multi-functional operating interface of the care-taking machine includes: muscle stretch sensor, multiplexer amplifying wave filter, analog-to-digital signal converter, image processing unit, and muscle pattern database and control bus. Aided by the present muscle template training method and potential image data collecting and processing method, it can become an interface that offers the user of a care-taking machine instantaneous and unlimited controllability of the machine, enabling such people, either sick or handicapped, to enjoy more convenience and better life.

8 Claims, 4 Drawing Sheets

MUSCLE STRETCH SENSOR

BACKGROUND OF THE INVENTION

1. Field of the Invention

The present invention relates to the methods and devices of a multi-functional operating interface for a care-taking machine.

2. Description of the Prior Art

Operation interface is a component indispensable and important to care-taking machines. What's more, the operational maneuverability of an interface affects the interaction between the user and the machine to every extent. By definition, the term care-taking machine used in this document refers to any kind of equipment that takes care of people and their lives, including electric wheelchair, living assistance and homecare equipment, computer interface, care-taking robots, etc., whose user can be the mentally or physically handicapped, children, the aged people, or even healthy people of all ages.

At the present stage, operation interfaces of care-taking machines generally fall into several categories by their means of giving commands: mechanical switch, operation stick, and body signal interface. The mechanical switches, including push button, breath switch, and touch button, offer only "on/off" operation mode. Due to its monotonous mode, the mechanical switch can offer only "yes/no" choice rather than complex options that must be standard for a care-taking machine such as an electric wheelchair. However, as such switches are easy to use and can be mounted on anywhere within a user's reach, they are often used for severely handicapped people.

Operation stick can provide some degrees of freedom of operation, so they are often used in an electric wheelchair or used as a computer interface. However, owing to its limited maneuverability, it is still inadequate for a sophisticated multi-functional care-taking machine that requires complicated operation system.

To tackle the above problem, the conventional solutions involve incorporating a combination of various operation interfaces, with each interface being responsible for a certain group of functions. This of course means that not only the functions that can be operated by severely handicapped people are significantly limited, but that even for the slightly handicapped, these systems are too complicate to operate.

The principle that underlies body signal type interfaces is by using sensing/detecting devices to obtain body signals reflected by the user (of a care-taking machine), which the system can analyze to determine the command to be given to the machine. The body signals used in the body signal type interface generally include: eye movement, brainwave (or electroencephalographic, EEG), electromyographic (EMG), and facial expression, etc. The eye movement signals are those signals and features of the movement of the eyeball, and the methods for collecting the eye movement signal include: Reflected Light, Electric Skin Potential, and Contact Lenses. This type interface can be used to control a care-taking machine with two or three degrees of freedom of operation, and its scope of use is roughly the same as that of the operation stick interface. However, it is mainly used for people who cannot move their hands.

Brain wave devices use electrodes attached on the scalp of a patient to detect the potential of his brain activities, which are further analyzed in order to perform the control activities thereby. Generally, the intensity of brainwave (or EEG) on the surface of the scalp ranges from 0 to 300 µV. For ease of understanding, EEGs are often divided into several sub-spectrums according to frequency: αwave (8~13 Hz), βwave (14~50 Hz), θwave (4~7 Hz), and δwave (less than 3.5 Hz). EEGs are most often used to analyze a patient's brainwave activity. If used in control devices, various stimulations must be used to obtain changes in α, β, θ and δwaves so that commands can be given. As such, the types of stimulations chosen are often determined by the modes of control to be used. Currently, the majority of such interfaces used in care-taking equipment make use of audio and video stimulations, such as the brain wave's response to stimulation signals is often slow, stimulations have to be maintained all the time. Besides, these interfaces offer only limited degree of freedom of operation. Similar to the eye movement interfaces, the EEG interfaces are mainly designed to be used by the person whose body movement is disabled.

The principle of EMG interfaces is that electrodes are attached to the skin to detect the electric potential of muscle activity, which is further analyzed to perform the control activity thereby. The frequency of a stronger EMG signal can reach 3000 Hz, with an intensity ranging from 0 to 2000 µV. EMG is mostly used to analyze a recipient's muscle actions and the muscle's ability to respond to stimulations. Used in operation interfaces, it has to be worked through a couple of electrodes, performed through the setting and detection of a threshold voltage, which together offers multi-degrees of freedom of motion and multi-task control of a care-taking machine. As is described, in order for the system to work, the user has to apply quite a number of electrodes on his body, causing much inconvenience and discomfort. Besides, EMG interfaces have to make allowances for false actions caused by inadequate/improper positioning of electrodes. Further, the recipient's skin has to be cleaned before applying electrodes—a quite troublesome and uncomfortable procedure.

Facial expression interfaces use Charge Coupled Device (CCD) camera to record the recipient's facial expressions, and the images are stored and classified and compared with those in an established database by means of an image-process method in order to determine what commands to be given. Through the use of such a control interface, a user can use various facial expressions to control a multi-functional care-taking machine having multi-degrees of freedom of motion. However, as image-processing techniques are at the core of these systems, the number of images to be stored and analyzed must be limited to gain immediate control of the machine. As a result, mistakes and wrong actions often occur, substantially limiting its freedom of control.

The following is a table summarizing the features of control interfaces used by prior art care-taking machines:

TABLE 1

CONTROL INTERFACES USED BY THE CONVENTIONAL CARE-TAKING MACHINES

| | | | body signals | | | |
|---|---|---|---|---|---|---|
| | mech. switches | joysticks | eye movement | brain waves | EMGs | facial expressions |
| freedom of control | low | low | low | low | medium | high |
| user disability | high | medium/low | high | high | high/medium | high/medium |
| techniques used | on/off | multi-directional on/off | reflection skin potential contact lens | spectrum analysis | magnitude of signals threshold voltage | image processing |
| instant controllability | high | high | medium | medium | medium | low |
| risk of mistakes | low | low | low | high | medium | medium |
| special Pretreatment | no | no | depending on methods of detection | special treatment must apply to where the detectors are attached, and stimulations must be used to obtain desired results | special treatment must applied to where the detectors are attached | No |

SUMMARY OF THE INVENTION

Figure 1:
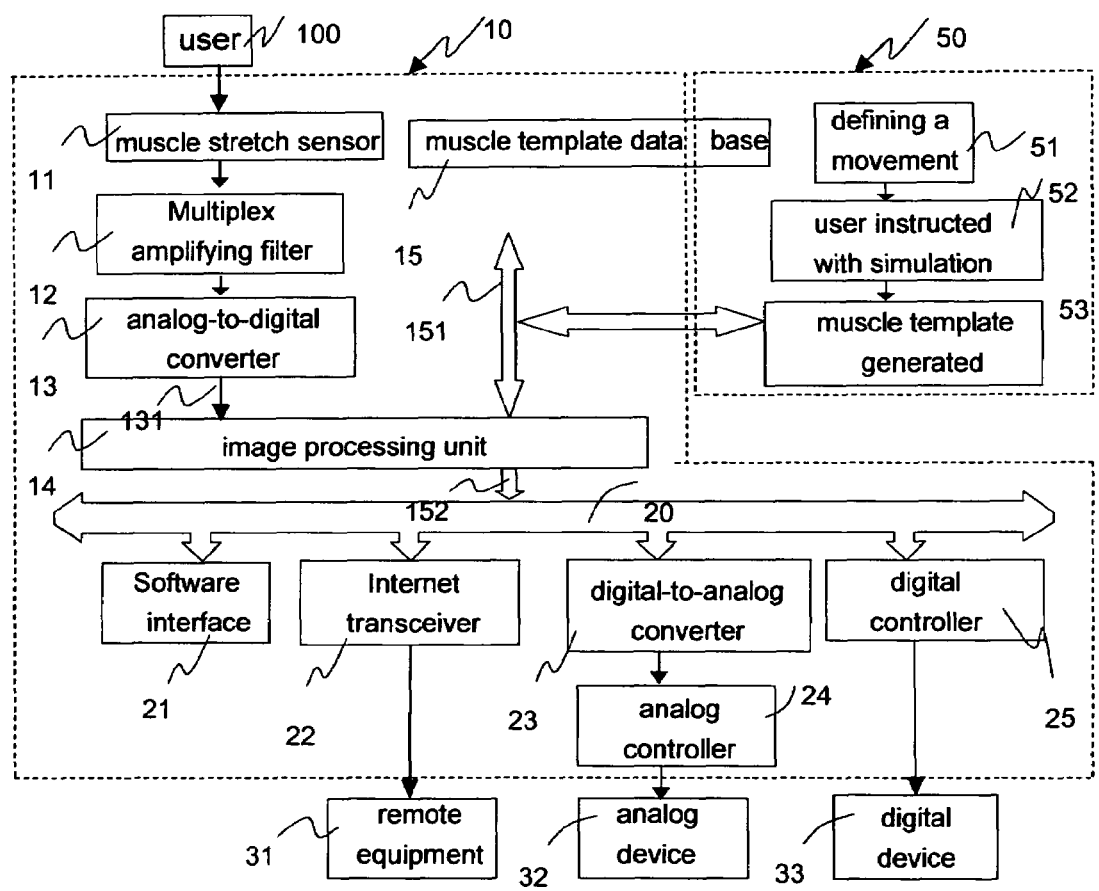
FIG. 1 shows the system structure of the multi-functional care-taking machine interface of the present invention.

To provide care-taking machines with high freedom of operation as well as instant control, while at the same time, reducing the risk of mistakes and eliminating the need for special pre-treatment, so that the disabled can be taken care of, the present invention hereby introduces a multi-functional interface and control device incorporating the most innovative detecting and signal processing techniques.

One object of the present invention is to provide a multi-functional interface and control device so that either a multi-functional care-taking machine or a combination of care-taking machines with different functions can be controlled through a single interface and device. Also, its discrete component structure allows use at different parts of the body.

Another object of the present invention is to provide a detecting method and device that provides the user of a care-taking machine an area allowing for the free moving of his body within a specified range. Through the detection device of the present invention, we can conduct any physical measurement regarding changes in strain, position, speed, and acceleration on any moving part of the body. Such measurements are not only to be used by the interface of the present invention, but can also be used to monitor the user's physical conditions.

Still another object of the present invention is to provide a special detection device and method with multiple-strain gauge. By attaching a plurality of strain gauges, which are adhesively attached to an appropriately flexible substrate, and multi-task scanning and amplifying circuit, it can measure the mechanical strain of a local area, providing data not only for the care-taking machine of the present invention, but also for other applications that need higher density strain analysis.

Further another object of the present invention is to provide a device and method for establishing potential images. Potential images are images that combine a multiple groups of potential signals and resemble gray scale images. These images can be obtained and grouped according to their feature. This device and method not only can provide data for the interface of the care-taking machine designed in accordance with the spirit of the present invention, but can be used in the processing and analyzing of massive potential signals, such as multi-channel brainwave signals or EMGs.

To achieve the above objects, the present invention uses specially designed detecting device and multiplexer scanning and amplifying circuit to do instant scanning of potential signals, establish potential images, and obtain and analyze their features so as to group them. Besides, through the same device, the present invention can establish a movement characteristics data and, by comparing the data with the characteristics of instant potential images obtained and conducting analysis and classification of the images, generate the control commands of the care-taking machine.

The special designed detecting device of the present invention is made of a plurality of strain gauges, which are adhesively attached to an appropriately flexible substrate. When the parts of the body to which the detectors are attached start movements, the flexible substrate will be pressed and squeezed, bringing the strain gauges into deformation. As quite a few strain gauges are used, a multiplexer scanning circuit must be added to the voltage amplifying the circuit in order that the use of amplifying circuit can be simplified. Besides, through detecting the multiple voltage signals via the instant scanning, the potential signals gathered can form potential images like grayscale images that can be analyzed by image processing techniques and grouped according to characteristics.

The movement characteristics database of the present invention can be a muscle template database, which stores characteristics of the user's muscle movements and commands generated by the training method of the template. It also provides the above muscle movement characters for the aforementioned image-processing unit to analyze and tally with existing characteristics data. The training method of the muscle template comprises three steps: 1. defining movements; 2. teaching stimulations to the user; and 3. generating muscle template.

The detection device of the present invention can be a muscle stretch sensor, comprising: a substrate, an adhesive layer, at least one strain gauge, a stimulation source, a signal bus, a plurality of cables, and a cover layer.

The multiplexer scanning and amplifying circuit of the present invention can be a multiplexer amplifying filter comprising: a bridge stimulation circuit, a detecting and amplifying circuit, a multiple address circuit, and an analog multiplexer and de-multiplexer circuit.

The potential image formation and processing techniques used by the present invention comprise the following steps: forming digital electric signals; constructing potential images; pre-processing image; grouping images; generating commands; and obtaining the next movement.

The multi-functional control interface of the present invention comprises: a muscle stretch sensor, a multiplexer amplifying filter, an analog-to-digital converter, an image-processing unit, a muscle template database and a control bus.

The present invention will be better understood from the detailed description with the aid of the illustrations given after it.

DETAILED DESCRIPTION OF THE INVENTION

FIG. 1 shows the device structure of the present invention. The multi-functional control interface of the care-taking machine designed in accordance with the spirit of the present invention 10 comprises: a plurality of muscle stretch sensor 11, which are used to detect the user's movement and generate electric signals and by which the user 100 can, through any moveable part of his body, exert control over a care-taking machine or other equipment through; a plurality of multiplexer amplifying filter 12, which are used to amplify/filter the electric signals of the muscle stretch sensor 11; an analog-to-digital converter 13, used to convert the analog signals outputted by the above multiplexer amplifying filter 12 into digital signals 131; an image processing unit 14, used to transform the above digital electric signals 131 into gray scale potential images which potential images are graphs, presented in black and white, and then analyze and group such images according to their characteristics; a muscle template database 15, used to store the characteristics 151 and movement commands 152 generated by the muscle template training method 50 as well to provide these characteristics 151 for the image processing unit 14 for future tallying and outputting movement commands 152; and a control bus 20, used to receive the above mentioned movement commands 152, and then transmit them to related interfaces, signal converting unit, or other control units, to exert control over the care-taking machine or other equipment; wherein the control bus 20 can be connected to software interfaces 21, internet transceiver 22, digital-to-analog converter 23, analog controller 24, digital controller 25, signal converting unit or other control unit, to control a particular care-taking machine or other equipment. These interfaces, signal converting components, or control components can also be parts of the multi-functional control interface 10 of the present invention.

In the above description, the user 100 refers to people of all age, regardless of their being healthy, disabled, children or the old. With the multi-functional control interface 10 of the spirit of the present invention, the user 100 can control the care-taking machine or any other equipment by exerting commands through any moveable part of his body.

As FIG. 1 shows, The method of the multi-functional control interface of the present invention comprises: a muscle template training method 50, a muscle template database 15 used to store characteristics 151 and movement commands 152 generated by the muscle template training method 50 and provide such characteristics 151 for the image processing unit 14 for further characteristics tallying.

The muscle template training method 50 comprises the following steps:

defining a movement 51—done by the trainer communicating with the trainee to define which characteristics of muscle pattern represent which specific control command;

instructing stimulations to the user 52—the trainer teaches the user how to stimulate/produce the characters as defined above; and generating muscle template 53—the muscle template is generated through the muscle stretch sensor 11 and image processing unit 14 of the present invention; the characteristics 151 and specific control commands 152 generated by the muscle template 53 are stored in the muscle template database 15.

The user 100 can also use the software interface 21 of the multi-functional control interface 10 of the present invention to operate computer games and other computer software; or work through internet transceiver to control remote equipment such as electric doors; or work through digital-to-analog converter 23 and analog controller to control analog devices such as an electrical wheel; or work through a digital controller 25 to control digital devices 33 such as LED signals.

Figures 1, 2:
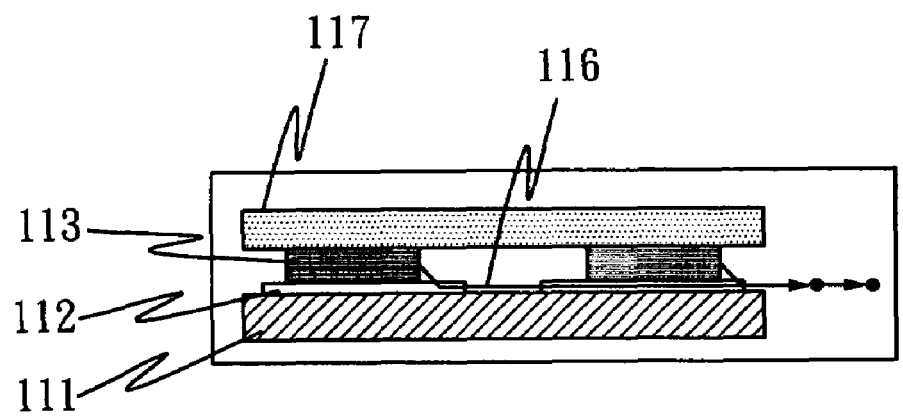
FIG. 2 shows how the muscle stretch sensor of the multi-functional care-taking machine control interface of the present invention works.
Figure 2:
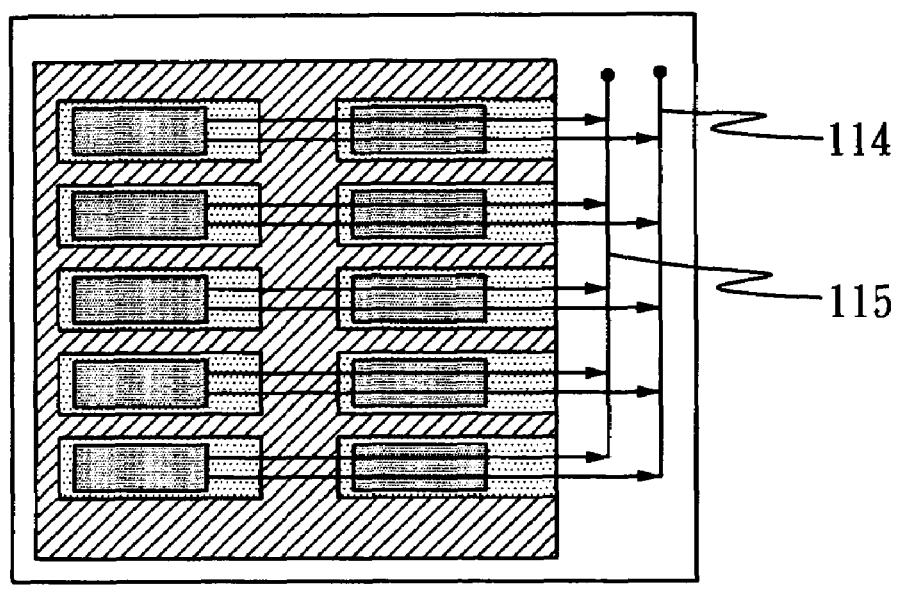

FIG. 2 shows the muscle stretch sensor 11 of the multi-functional control interface 10 of the care-taking machine designed in accordance with the spirit of the present invention. FIG. 2-1 shows the side view of the muscle stretch sensor 11 and FIG. 2-2 shows the top view of the muscle stretch sensor 11. The muscle stretch sensor 11 comprise: a sub-layer 111, made of a resilient material, and can be attached to any movable part of the user; an attachment layer 112, which can be attached to the surface of the above sub-layer 111, at least one strain gauge 113, attached on top of the above attachment layer 112, a stimulation source 114, which provides stimulations for the above strain gauges 113; a signal bus 115, which transmit electric signals detected by the strain gauge 113 to related components, a plurality of cables 116, which connect the strain gauge 113, with the stimulation source 114 and the signal bus 115; and a cover layer 117, which covers the attachment layer 112, the strain gauge 113, the stimulation source 114, the signal bus 115, the cables 116 to prevent them from contamination and damage; wherein the sub-layer 111 can be attached on any moveable parts of the user that when one such part moves, squeezing the muscle and deforming the strain gauges 113, signals showing the movements can be obtained. The number and arrangement of strain gauges 113 can be adjusted according to needs for convenience and freedom of control.

By connecting the above stimulation source 114 with the signal bus 115, the system transmits potential signals to the multiplexer amplifying filter 12, by which the detected strain signals are amplified/filtered. To simplify the use of amplifying circuit, we have to put a multiplexer scanning circuit on the voltage amplifying circuit.

Figure 3:
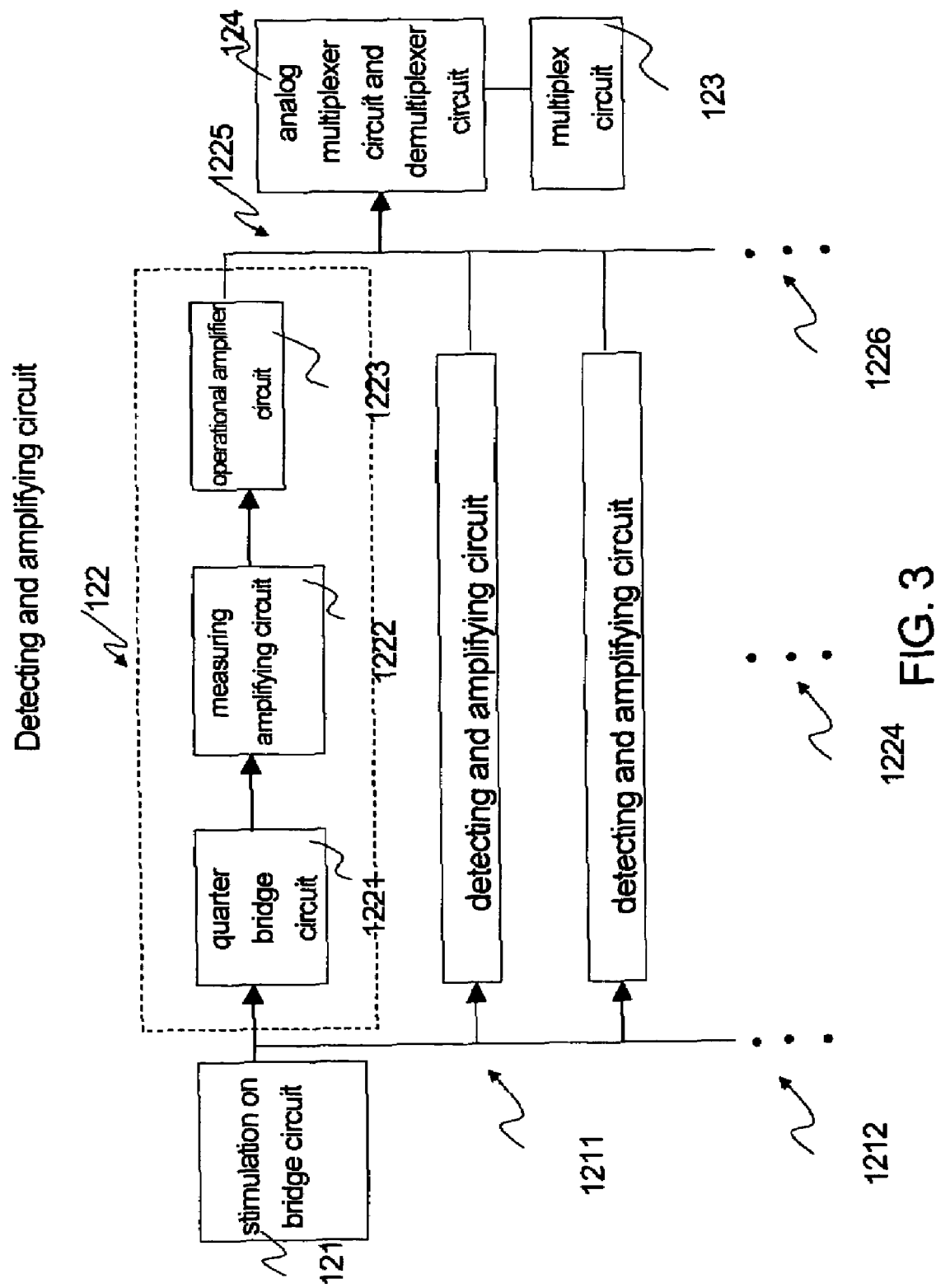
FIG. 3 shows the structure of the multiplexer scanning and amplifying circuit of the multi-functional care-taking machine control interface of the present invention.

FIG. 3 shows the structural view of the multiplexer amplifying filter 12 of the multi-functional control interface 10 of the present invention; the multiplexer amplifying filter 12 comprise: a stimulation (bridge) circuit 121, used to provide stimulation source for strain gauges 113; a detecting and amplifying circuit 122 used to detect muscle strains, convert electric signals, and amplify electric potential signals; a multiplex circuit 123, used to activate scanning; and an analog multiplexer and de-multiplexer circuit 124, used to receive commands from the multiplex circuit 123 to activate scanning.

wherein the above stimulation (bridge) circuit 121 can be made of Shunt Voltage Regular Diodes, such as LT1009CZ (Linear Technology), Single-Supply Precision OP, such as TLC272 (Texas Instruments), and High Output Current OP, such as TS921 (STMicroelectronics);

wherein the analog multiplexer and de-multiplexer circuit 124 and the multiplex circuit 123 can be made of CMOS Analog Multiplexers/Demultiplexers, such as CD4067B (Linear Technology);

wherein the detecting and amplifying circuit 122 further comprises: a quarter bridge circuit 1221, formed by connecting the above strain gauges 113 with a variable resistance bridge to convert mechanical strains into electric signals;

wherein the instrumentation amplifying circuit 1222 is mainly made of Instrumentation Amplifiers, such as AD62 (Analog Devices) and whose function is to amplify signals detected;

wherein the 1223 is mainly made of Operational Amplifiers, such as TLC272 (Texas Instruments), and whose function is to re-amplify signals detected;

wherein the stimulation source cables 1211 and the stimulation source cable's extended points 1212 mean that the stimulation source produced by the bridge stimulation circuit 121 can be used by more than one detecting and amplifying circuit 122;

wherein the extended points of the detecting and amplifying circuit 1224 mean that the system can parallel-use the detecting and amplifying circuit 122; and wherein the amplified signal cable 1225 and its extended points 1226 mean that the outputs of more than one Operational Amplifier circuit 1223 are transmitted to the analog multiplexer and de-multiplexer circuit 124 to wait for commands from the multiplex circuit to conduct scanning.

The deformation and electric signals as detected by the muscle stretch sensor 11 can be highly complicate and volatile. Even when there are definitions in the muscle template training method 50 regarding what muscle movement characteristics are to be interpreted as what control commands 152 and the user also uses movements defined by the muscle template to do the control, we still need to have some proper method to accurately identify a muscle template movement and its corresponding control command 152, so that the system can work properly as desired. We thus need a method that can process, analyze, and identify the electrical signals detected by the strain gauges 113.

Figure 4:
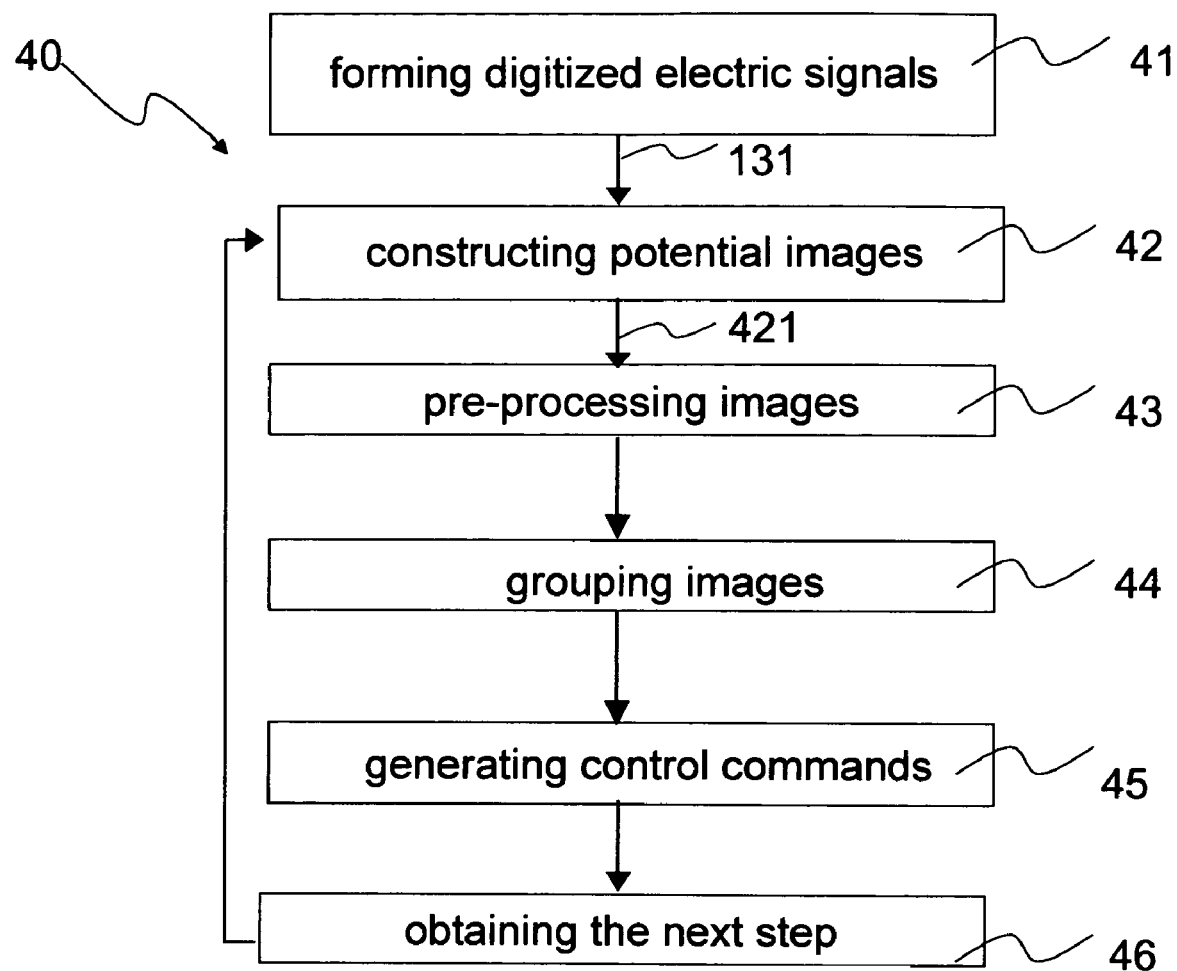
FIG. 4 shows constructing and processing processes of the potential image signals of the multi-functional care-taking machine control interface of the present invention.

FIG. 4 shows the method and steps by which the multi-functional control interface 10 of the present invention construct and process the potential image signals. The potential image signal construction and processing method 40 comprises the following steps:

forming digital electric signals 41: the detected signals processed by the multiplexer amplifying filter 12 and the analog-to-digital converter 13 to become digital electric signals 131;

potential image construction 42: image processing unit 14 received digital electric signals 131 and convert them into grey scale pixel signals forming specific potential images 421 which potential images 421 are graphs, presented in black and white; this is done by normalizing the irregularly or regularly shaped electric voltage signals into 256 categories and then re-arranging them in gray level dot matrix images;

pre-processing the images 43: characteristics of these potential images 421 are highlighted—for example, the gray level signals are "discretized" so that iso-potential lines and iso-potential points can be identified;

grouping the images 44: after the characteristics were highlighted, the potential images can be grouped, according to their characteristics, and tallied with those in the muscle template database 15. The user can, for example, use fuzzy neural network analysis to do the necessary characteristics grouping and tallying;

generating movement commands 45: after image grouping 44 and tallying with the muscle template database 15, movement commands 152 are given to the control bus 20, to conduct various controls of the care-taking machine; and obtaining the next step 46: after the above control cycle is completed, the next step goes back to the potential image construction step 42, starting the next control cycle.

The above method of potential image construction and processing 40 not only can be used to process signals detected by the strain gauges 113, but can be used to process, analyze, and identify massive electrical-potential signals, which are detected by other detectors and highly complicated, such as the signals of multi-channel EEGs and EMGs.

Compared with the prior art, the multi-functional control interface for care-taking machines developed by the present invention makes use of special detecting design and potential image processing techniques. As it provides better detection mobility, it is an interface adequate for controlling and operating a multi-functional care-taking machine. Besides, the multi-functional interface for a care-taking machine designed in accordance with the spirit of the present invention also excels over the prior art in terms of instant controllability and operation convenience—comparisons of which are shown in Table 2 below.

TABLE 2

COMPARISONS OF THE MULTI-FUNCTIONAL CARE-TAKING MACHINE INTERFACE OF THE PRESENT INVENTION AND THOSE OF THE PRIOR ART

| | multi-functional interface of the present invention | The prior art | |
| --- | --- | --- | --- |
| | | EMGs | facial expressions |
| detecting components | strain gauges | electrode | monitor/camera |
| what is detected | strains | voltage | images |
| density of components | high/medium | low | high |

TABLE 2-continued

COMPARISONS OF THE MULTI-FUNCTIONAL CARE-TAKING MACHINE INTERFACE OF THE PRESENT INVENTION AND THOSE OF THE PRIOR ART

|  | multi-functional interface of the present invention | The prior art | |
| --- | --- | --- | --- |
|  |  | EMGs | facial expressions |
| parts of body to be detected | Any moveable parts | Any moveable parts | face |
| freedom of control | high/medium | medium | high |
| user disability | high/medium | high/medium | high/medium |
| processing techniques | signal values image processing | signal values threshold voltage | image processing |
| instant controllability | medium | medium | low |
| risks of mistakes | medium/low | medium | medium |
| pre-treatment | no | parts of body where detectors are attached needs special treatment | no |

To sum up, the present invention not only is innovative in technological thinking, but does offer much more functions than the prior art, making it eligible for patents. The inventor hereby presents this application for your examiners esteemed evaluation.

As is understood by a person skilled in the art, the foregoing preferred embodiment of the present invention is an illustration, rather than a limiting description, of the present invention. It is intended to cover various modifications and similar arrangements included within the spirit and scope of the appended claims, the scope of which should be accorded the broadest interpretation so as to encompass all such modifications and similar structures.

What is claimed is:

1. A multi-functional care-taking machine interface that provides a user with operation, wherein the interface comprises:
   a muscle stretch sensor, comprising:
      a sub-layer, made of a resilient material, attached to any moveable parts of the user;
      an attachment layer, attached to a surface of said sub-layer;
      a plurality of strain gauges, attached on top of said attachment layer in an array, for detecting the deformation of any movable part of a body of the user to generate corresponding electric signals;
      a stimulation source, which provides stimulations for said strain gauges;
      a plurality of cables, which connect said strain gauges with said stimulation source and said signal bus; and
      a cover layer, which covers said attachment layer, said strain gauges, said stimulation source, said signal bus, and said cables to prevent contamination and damage;
   a multiplexer amplifying filter amplifying and filtering the electric signals generated by said strain gauges and output analog signals, wherein said multiplexer amplifying filter further comprises:
   a stimulation circuit providing said stimulation source;
   a detecting and amplifying circuit converting mechanical strains into electric signals and amplifying the electric signals, wherein said detecting and amplifying circuit further comprises:
      a quarter bridge circuit, converting the mechanical strains into electric signals;
      a detect amplifying circuit, which further comprises a plurality of detect amplifiers that amplify the detected electric signals; and
      an operational amplifier circuit, which further comprises an operational amplifier that re-amplifies the detected electric signals;
   a multiplex circuit activating scanning; and
   an analog multiplexer and de-multiplexer circuit receiving commands from the multiplex circuit to activate scanning;
   an analog-to-digital converter converting the analog signals outputted by said multiplexer amplifying filter into digital electric signals;
   an image processing unit arranging and converting said digital electric signal into gray level potential images, processing the images and highlighting their characteristics;
   a muscle template database storing movement characteristics, and passing the movement characteristics to said image processing unit for further tallying so that corresponding commands can be given; and
   a control bus receiving said commands, and passing said commands to any one of related interfaces, signal converting units, and other control units.

2. The multi-functional care-taking machine interface as claimed in claim 1, wherein said control bus is connected to software interfaces, internet transceivers, digital-to-analog converters, analog controllers, or digital controllers.

3. The multi-functional care-taking machine interface as claimed in claim 1, wherein a number and arrangement of said strain gauges is adjusted based on convenience and freedom of control.

4. The multi-functional care-taking machine interface as claimed in claim 1, wherein said stimulation circuit further comprises: at least a rectifier diode, at least a precision operational amplifier, and at least a high output current outputting operational amplifier.

5. The multi-functional care-taking machine interface as claimed in claim 1, wherein a multiplexer address circuit comprises said analog multiplexer and de-multiplexer circuit.

6. The multi-functional care-taking machine interface as claimed in claim 1, wherein the stimulation source produced by said stimulation circuit is used by said detecting and amplifying circuit.

7. The multi-functional care-taking machine interface as claimed in claim 1, wherein said detecting and amplifying circuit is utilized in parallel.

8. The multi-functional care-taking machine interface as claimed in claim 7, wherein outputs of said operational amplifier circuit is transmitted to the analog multiplexer and de-multiplexer circuit to wait for commands from the multiplexer address circuit to conduct scanning.

* * * * *